United States Patent
Dalko

(10) Patent No.: US 9,161,893 B2
(45) Date of Patent: *Oct. 20, 2015

(54) USE, AS ANTIDANDRUFF AGENT, OF (ETHOXYHYDROXYPHENYL) ALKYL KETONE OR ETHOXYHYDROXYALKYLPHENOL COMPOUNDS

(75) Inventor: Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/007,565

(22) PCT Filed: Mar. 30, 2012

(86) PCT No.: PCT/FR2012/050696
§ 371 (c)(1),
(2), (4) Date: Nov. 5, 2013

(87) PCT Pub. No.: WO2012/131274
PCT Pub. Date: Oct. 4, 2012

(65) Prior Publication Data
US 2014/0050678 A1 Feb. 20, 2014

Related U.S. Application Data

(60) Provisional application No. 61/472,665, filed on Apr. 7, 2011.

(30) Foreign Application Priority Data

Apr. 1, 2011 (FR) ..................... 11 52804

(51) Int. Cl.
| A61K 8/35 | (2006.01) |
| A61K 8/34 | (2006.01) |
| A61Q 5/00 | (2006.01) |
| A61Q 17/04 | (2006.01) |

(52) U.S. Cl.
CPC . *A61K 8/35* (2013.01); *A61K 8/347* (2013.01); *A61Q 5/006* (2013.01); *A61Q 17/04* (2013.01)

(58) Field of Classification Search
None
See application file for complete search history.

(56) References Cited

U.S. PATENT DOCUMENTS

| 8,765,101 B2 * | 7/2014 | Marion et al. ............. 424/59 |
| 2003/0017997 A1 * | 1/2003 | Yokota et al. ............. 514/25 |
| 2006/0216252 A1 * | 9/2006 | Baschong et al. .......... 424/62 |
| 2007/0116664 A1 * | 5/2007 | Gonen ...................... 424/74 |
| 2012/0263768 A1 * | 10/2012 | Marion et al. ............ 424/401 |
| 2014/0057997 A1 * | 2/2014 | Chevalier et al. .......... 514/772 |

OTHER PUBLICATIONS

Agarwal et al. Insect growth inhibition, antifeedant and antifungal activity of compounds isolated/derived from Zingiber officinale Roscoe (ginger) rhizomes. Pest Manag Sci 57:289-300 (2001).*
Chhavi et al. Potential of Herbals as Antidandruff Agents. IRJP 2(3) 2011:16-18.*

* cited by examiner

*Primary Examiner* — Robert A Wax
*Assistant Examiner* — Olga V Tcherkasskaya
(74) *Attorney, Agent, or Firm* — Novak Druce Connolly Bove + Quigg LLP

(57) ABSTRACT

The present invention relates to the use, as an antidandruff agent, of a compound of formula:

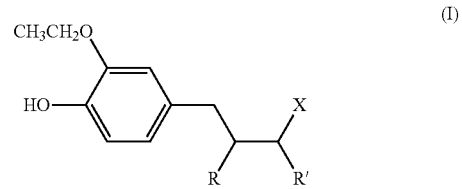

in which:
R1 represents a hydrogen atom or a hydrocarbon-based radical;
R' represents a $C_1$-$C_{18}$ hydrocarbon-based radical, optionally substituted with a hydroxyl group;
C—X represents C=O or CH—OH.

20 Claims, No Drawings

USE, AS ANTIDANDRUFF AGENT, OF (ETHOXYHYDROXYPHENYL) ALKYL KETONE OR ETHOXYHYDROXYALKYLPHENOL COMPOUNDS

CROSS REFERENCE TO RELATED APPLICATIONS

This application is a National Phase filing under 35 U.S.C. §371 of PCT/FR2012/050696 filed on Mar. 30, 2012; and this application claims priority to Application No. 1152804 filed in France on Apr. 1, 2011; which claims the benefit of U.S. Provisional Application No. 61/472,665 filed on Apr. 7, 2011; the entire contents of all are hereby incorporated by reference.

TECHNICAL FIELD

The present invention relates to the use of 4-(3-ethoxy-4-hydroxyphenyl)alkyl ketone or 2-ethoxy 4-hydroxyalkylphenol compounds, which may be derived from vanillin, as an antidandruff agent, in particular in the cosmetic treatment of dandruff conditions linked to the excessive proliferation of yeasts of the *Malassezia* genus on the scalp. The invention also relates to a cosmetic treatment method intended to eliminate and/or reduce dandruff, in particular dandruff caused by yeasts of the *Malassezia* genus, which employs said compounds.

BACKGROUND ART

Dandruff problems affect up to 50% of the world's population. They affect both men and women and are perceived as having a very negative psychosocial impact. The appearance of dandruff is bothersome both aesthetically and because of the trouble it causes (itching, redness, etc.), and as such many people confronted with this problem to variable degrees wish to eliminate it efficiently and permanently.

Dandruff corresponds to an excessive and visible desquamation of the scalp resulting from the excessively rapid multiplication of the epidermal cells and from their abnormal maturation. This phenomenon may be caused in particular by microtraumas of physical or chemical nature, such as excessively aggressive hair treatments, extreme climatic conditions, nervousness, diet, fatigue and pollution, but it has been demonstrated that dandruff conditions usually result from a disorder of the microflora of the scalp and are more particularly due to the excessive colonization of a fungus belonging to the family of yeasts of the *Malassezia* genus (previously known as *Pityrosporum ovale*) and which is naturally present on the scalp.

Many antidandruff treatments have been developed with the main objective of eradicating *Malassezia* yeasts from the scalp. Thus, the activity of the major antidandruff active agents of today, such as zinc pyrithione, piroctone olamine or selenium disulfide, is based mainly on their fungicidal property. However, these antidandruff agents are not completely satisfactory in terms of effectiveness (immediate effectiveness or duration of the effect) and/or in terms of impact on the environment.

BRIEF SUMMARY OF THE DISCLOSURE

The aim of the present invention is to provide antidandruff agents which are not irritant to the skin or the scalp, and which are as effective as the known antidandruff agents, while at the same time having a more favourable impact in terms of the environment (low bioaccumulation and good biodegradability in particular) and/or having good stability over time (in particular after storage of a cosmetic composition containing it, after 2 months at ambient temperature or at 45° C.) and/or having good cosmetic properties such as good skin tolerance. Another aim of the invention is to provide active agents which make it possible to re-establish the ecoflora of the scalp and in particular to prevent excessive colonization of the scalp by *Malassezia* sp.

DETAILED DESCRIPTION OF THE DISCLOSURE

The applicant has now found, surprisingly, that the use of at least one compound of formula (I) makes it possible to effectively treat dandruff conditions, in particular those associated with the proliferation of yeasts of the *Malassezia* genus, and to overcome the disadvantages of the prior art.

It has been observed that, by employing the compounds of formula (I), it is possible to remove and/or reduce the number of yeasts of the *Malassezia* genus, the amount of dandruff, and also the itching and the redness of the scalp.

A subject of the present invention is therefore the use, as an antidandruff agent, of at least one compound of formula (I):

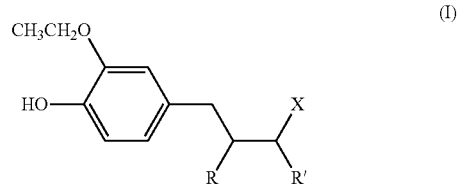

in which:
R represents a hydrogen atom, or a linear or branched, saturated or unsaturated (alkyl or alkenyl), $C_1$-$C_6$ hydrocarbon-based radical;
R' represents a linear or branched, saturated or unsaturated (alkyl or alkenyl), $C_1$-$C_{18}$ hydrocarbon-based radical, optionally substituted with a hydroxyl group; —C—X represents C=O or CH—OH.

In particular, the invention relates to the use of compounds of formula (I) for treating the dandruff conditions associated with the proliferation of yeasts of the *Malassezia* genus on the scalp.

The compounds according to the invention therefore correspond to the formula (I):

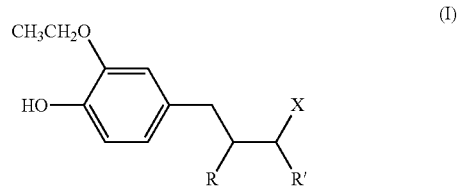

in which:
R represents a hydrogen atom, or a linear or branched, saturated or unsaturated (alkyl or alkenyl), $C_1$-$C_6$ hydrocarbon-based radical;
R' represents a linear or branched, saturated or unsaturated (alkyl or alkenyl), $C_1$-$C_{18}$ hydrocarbon-based radical, optionally substituted with a hydroxyl group; —C—X represents C=O or CH—OH.

Preferably, R represents H, methyl or ethyl.

Preferably, R' represents a saturated $C_1$-$C_6$, or unsaturated $C_2$-$C_6$, linear hydrocarbon-based radical, optionally substituted with a hydroxyl group.

Preferably, the compounds correspond to formula (I), in which:

C—X represents C=O, R=H and R' represents a linear $C_1$-$C_6$ alkyl radical, optionally substituted with an OH; preferably, R'=methyl or ethyl; or else C—X represents CH—OH, R=H and R' represents a linear $C_1$-$C_6$ alkyl radical, optionally substituted with an OH; preferably, R'=methyl or ethyl.

Mention may in particular be made of the following compounds:

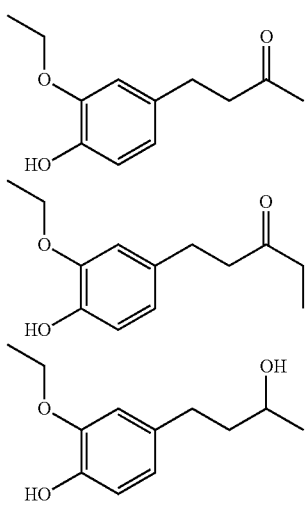

A mixture of compounds of formula (I) may, of course, be used.

The compound which is particularly preferred is:

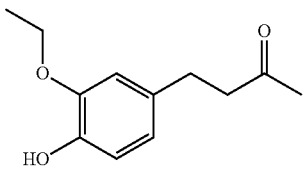

The compounds of formula (I) can be readily prepared by those skilled in the art on the basis of their general knowledge. Mention may be made in particular of the following bibliographic references: J. Asian Natural Products Research, 2006, 8(8), 683-688; Helv. Chimica Acta, 2006, 89(3), 483-495; Chem. Pharm. Bull., 2006, 54(3), 377-379; and Bioorg. J. Med. Chem. Lett., 2004, 14(5), 1287-1289.

They may thus be prepared from ethylvanillin, in the following manner:

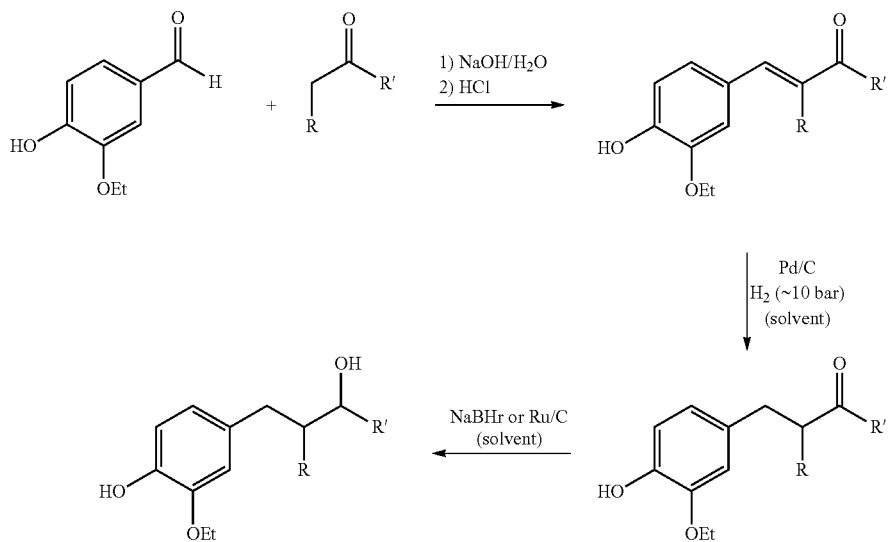

The compounds of formula (I) with C—X representing CHOH can be obtained by reduction of the corresponding compounds in which C—X represents C=O, for example by reduction with Ru/C or $NaBH_4$.

The compounds of formula (I), alone or as a mixture, can be used in a proportion of from 0.1% to 10% by weight, in particular 0.5% to 5% by weight, relative to the weight of the cosmetic composition.

The cosmetic compositions according to the invention comprise a cosmetically acceptable medium, i.e. a medium that is compatible with keratin materials, such as the skin of the face or of the body, the lips, the hair, the eyelashes, the eyebrows and the nails.

The compounds according to the invention are generally used by topical application. In particular, they can be used as antidandruff agents in a cosmetic composition that can be in any of the galenical forms normally used for topical application.

The cosmetic composition used according to the invention can be a hair composition which can be rinsed-out or left-in. Said hair composition is preferably a shampoo, a cream, a foam (aerosol or non-aerosol), a paste, a gel, an emulsion, a lotion or a stick. Preferably, the cosmetic composition is a shampoo or a gel.

The cosmetic composition used according to the invention generally comprises a cosmetically acceptable medium. Preferably, said medium comprises water and/or one or more cosmetically acceptable organic solvents. The organic solvents can be chosen from linear or branched $C_1$-$C_6$ monoalcohols, such as ethanol, isopropanol, tert-butanol or n-butanol; polyols such as glycerol, propylene glycol, hexylene glycol (or 2-methyl-2,4-pentanediol) and polyethylene glycols; polyol ethers, for instance dipropylene glycol monomethyl ether; and mixtures thereof. Preferably, the cosmetic composition used according to the invention comprises an amount of organic solvents ranging from 0.05% to 60%, preferably from 0.5% to 50% and even better still from 1% to 40% by weight, relative to the total weight of the cosmetic composition.

The cosmetically acceptable medium can also advantageously comprise thickeners; surfactants chosen from anionic, cationic, non-ionic and/or amphoteric or zwitterionic surfactants; conditioning agents; silicones; agents for combating hair loss; other antidandruff agents; oxidizing agents, vitamins; waxes; sunscreens; coloured or colourless inorganic or organic pigments; dyes; pearlescent and opacifying agents; sequestering agents; plasticizers; fragrances; preservatives. Of course, those skilled in the art will take care to choose this or these optional additional compound(s) and/or the amount thereof in such a way that the advantageous properties of the composition according to the invention are not, or not substantially, detrimentally affected by the envisaged addition.

A subject of the invention is also a cosmetic treatment method intended to eliminate and/or reduce dandruff, in particular dandruff caused by yeasts of the *Malassezia* genus, characterized in that it comprises the application, to the hair and/or the scalp, of at least one compound of formula (I) or else of a cosmetic composition comprising at least one compound of formula (I). The cosmetic composition can then be optionally rinsed out with water. Preferably, this cosmetic treatment method is repeated at the rate of at least twice weekly.

The invention is illustrated in greater detail in the following examples.

EXAMPLE 1

Compound tested:

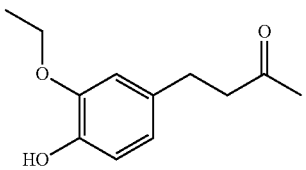

A solution containing 2% by weight of test compound is prepared in "modified Leeming and Notman liquid (MLNA)" in the following way: 0.2048 g of test compound is weighed out into qs for 10 ml of modified Leeming and Notman liquid; solubilization is carried out by heating and the use of ultrasound.

The solutions of test product are twice as concentrated as the final test concentration, in order to take into account the dilution when they are brought into contact with the *Malassezia* suspension.

One of the previously prepared solutions at 2% is diluted to ½ in modified Leeming and Notman liquid, so as to finally obtain a test concentration of 0.5%; the other solution is used as it is (at 2%) so as to finally obtain a test concentration of 1%.

The *Malassezia* strains are brought into contact according to the table below:

|  | Growth control | Test composition |
|---|---|---|
| Strain | 0.5 ml | 0.5 ml |
| Test solution | — | 0.5 ml |
| MLNA medium | 0.5 ml | — |

The mixture is stirred and deposited at the surface of the MLNA agar. It is spread, with a sterile scraper, over the entire surface before recovering the excess. It is left to incubate for at least 5 days at 30° C.

The antifungal effect of the compound is evaluated via the absence of growth of the *Malassezia* strain tested. This inhibition is evaluated relative to the growth control. The inhibitions are scored from 0 to 3 via assessment of the density of the culture at the surface of the agar, in comparison with the growth control, in the following way:

| Score | Inhibition | Interpretation |
|---|---|---|
| 3 | 100% | No growth |
| 2 | 75% | Growth < in the control dish |
| 1 | 25% | Growth < in the control dish |
| 0 | 0% | Growth comparable to the control dish |

The following results are obtained:

|  | *Malassezia restricta* | *Malassezia globosa* |
|---|---|---|
| Growth control | Culture dense | Culture dense |
| Compound tested at 1% | 3 | 3 |
| Compound tested at 0.5% | 3 | 1 |

The compound at 1% completely inhibits the growth of the two *Malassezia* strains. It is also very effective at 0.5% on *Malassezia restricta*, and weakly on *Malassezia globosa*.

The invention claimed is:
1. An antidandruff cosmetic treatment method, which comprises applying to the hair and/or the scalp of a person having dandruff, as an antidandruff agent, at least one compound of formula (I):

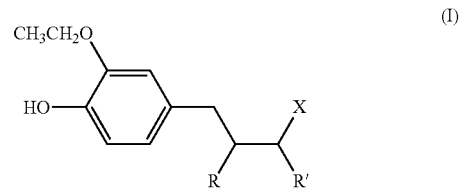

wherein R represents a hydrogen atom, or a linear or branched, saturated or unsaturated $C_1$-$C_6$ hydrocarbon-based radical; R' represents a linear or branched, saturated or unsaturated $C_1$-$C_{18}$ hydrocarbon-based radical, or wherein the $C_1$-$C_{18}$ hydrocarbon-based radical is substituted with a hydroxyl group; and C—X represents C=O or CH—OH.

2. The method according to claim 1, in which R represents H, methyl or ethyl.

3. The method according to claim 1, wherein R' represents a saturated $C_1$-$C_6$ or unsaturated $C_2$-$C_6$ linear hydrocarbon-based radical, or wherein said hydrocarbon-based radical is substituted with a hydroxyl group.

4. The method according to claim 1, wherein the compounds correspond to formula (I), in which:
   C—X represents C=O, R represents a hydrogen atom and R' represents a linear $C_1$-$C_6$ alkyl radical optionally substituted with an OH; or else
   C—X represents CH—OH, R represents a hydrogen atom and R' represents a linear $C_1$-$C_6$ alkyl radical optionally substituted with an OH.

5. The method according to claim 1, wherein C—X represents C=O; R represents a hydrogen atom, and R' represents methyl or ethyl; or C—X represents CH—OH; R represents a hydrogen atom, and R' represents methyl.

6. The method according to claim 1, wherein C—X represent C=O; R represents a hydrogen atom, and R' represents methyl.

7. The method according to claim 1, wherein the compound of formula (I), alone or as a mixture, is present in a proportion of from 0.1% to 10% by weight relative to the weight of the cosmetic composition.

8. The method according to claim 1, wherein the compound of formula (I), alone or as a mixture, is present in a cosmetic hair composition comprising a cosmetically acceptable medium.

9. The method according to claim 1, wherein the compound of formula (I), alone or as a mixture, is present in a cosmetic composition comprising a cosmetically acceptable medium which comprises at least one ingredient chosen from: water, linear or branched $C_1$-$C_6$ monoalcohols; polyols; polyol ethers; thickeners; surfactants chosen from anionic, cationic, non-ionic and/or amphoteric or zwitterionic surfactants; conditioning agents; silicones; agents for combating hair loss; other antidandruff agents; oxidizing agents, vitamins; waxes; sunscreens; coloured or colourless inorganic or organic pigments; dyes; pearlescent and opacifying agents; sequestering agents; plasticizers; fragrances; preservatives.

10. The method according to claim 1, for treating the dandruff conditions associated with the proliferation of yeasts of the *Malassezia* genus on the scalp.

11. The method according to claim 2, wherein R' represents a saturated $C_1$-$C_6$ or unsaturated $C_2$-$C_6$ linear hydrocarbon-based radical, or wherein said hydrocarbon-based radical is substituted with a hydroxyl group.

12. The method according to claim 11, wherein the compounds correspond to formula (I), in which:
   C—X represents C=O, R represents a hydrogen atom and R' represents a linear $C_1$-$C_6$ alkyl radical optionally substituted with an OH; or else
   C—X represents CH—OH, R represents a hydrogen atom and R' represents a linear $C_1$-$C_6$ alkyl radical optionally substituted with an OH.

13. The method according to claim 4, wherein R' represents methyl or ethyl.

14. The method according to claim 2, wherein the compounds correspond to formula (I), in which:
   C—X represents C=O, R represents a hydrogen atom and R' represents a linear $C_1$-$C_6$ alkyl radical optionally substituted with an OH; or else
   C—X represents CH—OH, R represents a hydrogen atom and R' represents a linear $C_1$-$C_6$ alkyl radical optionally substituted with an OH.

15. The method according to claim 3, wherein the compounds correspond to formula (I), in which:
   C—X represents C=O, R represents a hydrogen atom and R' represents a linear $C_1$-$C_6$ alkyl radical optionally substituted with an OH; or else
   C—X represents CH—OH, R represents a hydrogen atom and R' represents a linear $C_1$-$C_6$ alkyl radical optionally substituted with an OH.

16. The method according to claim 1, wherein the compound of formula (I), alone or as a mixture, is present in a proportion of from 0.5% to 5% by weight, relative to the weight of the cosmetic composition.

17. The method according to claim 2, wherein the compound of formula (I), alone or as a mixture, is present in a proportion of from 0.1% to 10% by weight, relative to the weight of the cosmetic composition.

18. The method according to claim 3, wherein the compound of formula (I), alone or as a mixture, is present in a proportion of from 0.1% to 10% by weight, relative to the weight of the cosmetic composition.

19. The method according to claim 4, wherein the compound of formula (I), alone or as a mixture, is present in a proportion of from 0.1% to 10% by weight, relative to the weight of the cosmetic composition.

20. The method according to claim 5, wherein the compound of formula (I), alone or as a mixture, is present in a proportion of from 0.1% to 10% by weight, relative to the weight of the cosmetic composition.

* * * * *